United States Patent [19]
Toriba et al.

[11] Patent Number: 5,626,834
[45] Date of Patent: May 6, 1997

[54] SNAKE-CONTROLLING AGENT

[75] Inventors: Michihisa Toriba, Takasaki; Kenji Tsuda, Musashino; Satoshi Senbo; Yoshiaki Kosuge, both of Takarazuka; Hiroshi Fukui, Yokohama; Yoichiro Tsubaki, Tokyo, all of Japan

[73] Assignee: Sumitomo Chemical Company, Limited, Osaka, Japan

[21] Appl. No.: 921,109

[22] Filed: Jul. 30, 1992

[30] Foreign Application Priority Data

Oct. 17, 1991 [JP] Japan ..................... 3-269341

[51] Int. Cl.$^6$ ................................ A01N 25/06
[52] U.S. Cl. ................. 424/45; 424/46; 424/405; 560/124; 514/531
[58] Field of Search ............... 424/45, 46, 405; 560/124; 514/531

[56] References Cited

FOREIGN PATENT DOCUMENTS

| 0148625 | 7/1985 | European Pat. Off. . |
| 0256855 | 2/1988 | European Pat. Off. . |
| 0477676 | 4/1992 | European Pat. Off. . |
| 2157202 | 6/1990 | Japan . |

OTHER PUBLICATIONS

"The Merck Index" Compound 244 (1983) Published by Merck & Co, Inc.

"The Agrochemicals Handbook" Second edition pp. 87–88 (1987).

*Primary Examiner*—Jyothsna Venkat
*Attorney, Agent, or Firm*—Watson Cole Stevens Davis, P.L.L.C.

[57] ABSTRACT

A snake-controlling agent contains at least one pyrethroid compound as an active ingredient. It is used for controlling snakes. According to the present invention, the effective controlling of snakes is possible by utilizing the snake-controlling property of pyrethroid compounds.

7 Claims, No Drawings

SNAKE-CONTROLLING AGENT

The present invention relates to a snake-controlling agent and a method for controlling snakes by using the same.

The dangers and threats of snake bites are more often encountered in the temperate to tropical regions of the earth, particularly to workers in agriculture and forestry, and to members of the military forces, among others. These dangers are of particular concern where the snakes are poisonous, and bites by poisonous snakes are often fatal. Snakes also cause other dangers or risks; they have been known to climb utility poles and short-circuit power and transmission lines, which have caused interruptions in the operations of life-supporting medical devices and electronic machines including computers.

The residents, workers in agriculture and forestry, power supplying industries and military in regions inhabited by poisonous snakes have made some attempts to counter such dangers, such as providing smooth, slippery surfaces for buildings with a coating, grease and/or available snake repellents to prevent the passage of snakes, or have equipped utility poles with ring barriers. The results therefrom, however, have not been satisfactory.

Capturing and destroying snakes have also been conducted on various scales. However, this obviously involves considerable man-power and the risk of snake bites to the men of the capturing teams. Moreover, the results have not been really effective, often inefficient.

Thus, the advent of a truly and quickly effective snake-controlling agent has been strongly desired for the prevention of snake bites.

In view of the circumstances, the present inventors have extensively studied to develop a snake-controlling agent showing an immediate and outstanding effect. As a results, they have found that pyrethroid compounds are superior in their snake-controlling effect and have attained to the present invention based on the finding.

According to the present invention, there are provided a snake-controlling agent comprising at least one pyrethroid compound as an active ingredient and a method for controlling snakes using the same.

Specific examples of the pyrethroid compounds usable in the present invention are listed below by the chemical name together with the number for identifying the compound.

Compounds containing a cyclopentenolone skeleton:

(1) 2-methyl-4-oxo-3-(2-propynyl)cyclopent-2-enyl chrysanthemate, (2) (S)-2-methyl-4-oxo-3-(2-propynyl)cyclopent-2-enyl (1R)-cis,trans-chrysanthemate (common name: prallethrin), (3) 2-methyl-4-oxo-3-(2-propenyl)cyclopent-2-enyl chrysanthemate (common name: allethrin), (4) 2-methyl-4-oxo-3-(2-propenyl)cyclopent-2-enyl (1R)-cis,trans-chrysanthemate (common name: d-allethrin), (5) (RS)-2-methyl-4-oxo-3-(2-propenyl)cyclopent-2-enyl (1R)-trans-chrysanthemate (common name: bioallethrin), (6) (S)-2-methyl-4-oxo-3-(2-propenyl)cyclopent-2-enyl (1R)-trans-chrysanthemate (common name: S-bioallethrin), (7) 2-methyl-4-oxo-3-(2-furfuryl)cyclopent-2-enyl chrysanthemate (common name: furethrin), (8) 2-methyl-4-oxo-3-(2-propenyl)cyclopent-2-enyl 2,2,3,3-tetramethylcyclopropanecarboxylate (common name: terallethrin), (9) natural pyrethrins (common name), and the like;

(10) 5-(2-propynyl)furfuryl chrysanthemate (common name: furamethrin),

(11) 5-(2-propynyl)furfuryl (1R)-cis,trans-chrysanthemate,

(12) 5-benzyl-3-furylmethyl chrysanthemate (common name: resmethrin),

(13) 5-benzyl-3-furylmethyl (1R)-cis,trans-chrysanthemate,

(14) 3-phenoxybenzyl chrysanthemate (common name: phenothrin),

(15) 3-phenoxybenzyl (1R)-cis,trans-chrysanthemate (common name: d-phenothrin),

(16) 3-phenoxybenzyl 3-(2,2-dichlorovinyl)-2,2-dimethylcyclopropanecarboxylate (common name: permethrin),

(17) α-cyano-3-phenoxybenzyl chrysanthemate,

(18) α-cyano-3-phenoxybenzyl (1R)-cis,trans-chrysanthemate (common name: cyphenothrin),

(19) α-cyano-3-phenoxybenzyl 3-(2,2-dichlorovinyl)-2,2-dimethylcyclopropanecarboxylate (common name: cypermethrin),

(20) α-cyano-3-phenoxybenzyl 2-(4-chlorophenyl)-3-methylbutyrate (common name: fenvalerate),

(21) (S)-α-cyano-3-phenoxybenzyl (S)-2-(4-chlorophenyl)-3-methylbutyrate (common name: esfenvalerate),

(22) 1-ethynyl-2-methyl-2-pentenyl chrysanthemate,

(23) 1-ethynyl-2-methyl-2-pentenyl (1R)-cis,trans-chrysanthemate (common name: empenthrin),

(24) 3,4,5,6-tetrahydrofuthalimidomethyl chrysanthemate (common name: tetramethrin),

(25) 3,4,5,6-tetrahydrofuthalimidomethyl (1R)-cis,trans-chrysanthemate (common name: d-tetramethrin),

(26) α-cyano-4-fluoro-3-phenoxybenzyl 3-(2,2-dichlorovinyl)-2,2-dimethylcyclopropanecarboxylate (common name: cyfluthrin),

(27) α-cyano-3-phenoxybenzyl 3-(2,2-dibromovinyl)-2,2-dimethylcyclopropanecarboxylate,

(28) (S)-α-cyano-3-phenoxybenzyl (1R)-cis-3-(2,2-dibromovinyl)-2,2-dimethylcyclopropanecarboxylate (common name: deltamethrin),

(29) 2,3,5,6-tetrafluorobenzyl 3-(2,2-dichlorovinyl)-2,2-dimethylcyclopropanecarboxylate,

(30) 2,3,5,6-tetrafluorobenzyl (1R)-trans-3-(2,2-dichlorovinyl)-2,2-dimethylcyclopropanecarboxylate, (common name: benfluthrin),

(31) 2-(4-ethoxyphenyl)-2-methylpropyl 3-phenoxybenzyl ether (common name: ethofenprox).

Of these, the compounds having a cyclopentenolone skeleton are preferable from the viewpoint of snake-controlling effect. The compounds (1), (2), (3), (4), (5), (6), (7), (8) and (9) are more preferable. The compound (2) is most preferable.

For the snake-controlling agent of the present invention, each of the above-listed active ingredients may be used as it is. However, it is usually used after having been formulated into various formulations by mixing each of the above-listed active ingredients with a solid carrier, a liquid carrier, or a gaseous carrier. If necessary, surfactants and the other auxiliaries for formulation may be added to the formulations. These formulations include, for example, aerosols, liquefied carbon dioxide gas formulation, dusts, oil formulations, emulsifiable concentrates, fumigants, smoking formulations. Here, a suitable, formulation form may be selected depending on the area, method, etc. for application.

The solid carrier used for formulation includes, for example, fine powders or granules of clays (e.g. kaolin clay, diatomaceous earth, synthetic hydrated silicon dioxide, bentonite, and acid clay), talcs, ceramics, other inorganic minerals (e.g. sericite, quartz, sulfur, activated carbon, calcium carbonate and hydrated silica), chemical fertilizers (e.g. ammonium sulfate, ammonium phosphate, ammonium nitrate, urea and ammonium chloride).

The liquid carrier includes, for example, water, alcohols (e.g. methanol and ethanol), ketones (e.g. acetone and methyl ethyl ketone), ethers (e.g. tetrahydrofuran and dioxane), aliphatic hydrocarbons (e.g. hexane, kerosene, paraffin and petroleum benzine), aromatic hydrocarbons (e.g. benzene, toluene and xylene), esters (e.g. ethyl acetate and butyl acetate), halogenated hydrocarbons (e.g. dichloroethane, trichloroethane and carbon tetrachloride), liquefied carbon dioxide gas.

The gaseous carrier, i.e., propellant, includes for example, freon gas, propane gas, butane gas, LPG (liquefied petroleum gas), dimethyl ether and carbon dioxide gas.

The surfactant includes, for example, alkyl sulfates, alkyl sulfonates, alkylaryl sulfonates, alkyl aryl ethers and their polyoxyethylenated products, polyethylene glycol ethers, polyhydric alcohol esters and sugar alcohol derivatives.

The auxiliaries for formulation such as fixing agents and dispersants include, for example, casein, gelatin, polysaccharides (e.g. starch powder, gum arabic, cellulose derivatives and alginic acid), lignin derivatives, bentonite, saccharides, synthetic water-soluble polymers (e.g. polyvinyl alcohol, polyvinyl pyrrolidone and polyacrylic acids). As stabilizers, there can be exemplified PAP (acidic isopropyl phosphate), BHT (2,6-di-tert-butyl-4-methylphenol), BHA (a mixture of 2-tert-butyl-4-methoxyphenyl and 3-tert-butyl-4-methoxyphenol), vegetable oils, mineral oils, surfactants, and fatty acids or their esters.

Among the various forms of formulations, it has been found that the aerosol-type sprayer is particularly preferable. (Besides being highly easy-to-use, the aerosol type sprayer is adaptable to counter a sudden appearance of snakes.) Because some snakes attack or jump from a crouching or recoiling position to a distance of one meter or longer, such as in the case of habu, it should be desirable to have an aerosol sprayer with an effective spraying distance of 2 meters or longer.

The concentration of the active ingredient(s) in the above-mentioned formulations may be determined according to the type of the formulation, the method of the application and the place of the application. However, it is usually between 0.001% by weight and 50% by weight, preferably between 0.01% by weight and 20% by weight.

If necessary, one or more synergists can be added to the snake-controlling agent of the present invention. Specific examples of the preferable synergists are listed below by the chemical name together with the alphabetical symbol identifying the compound.

(A) bis(2,3,3,3-tetrachloropropyl)ether (S-421), (B) N-(2-ethylhexyl)bicyclo[2.2.1]hept-5-en-2,3-dicarboxyimide (MGK-264), (C) isobornyl thiocyanoacetate (IBTA), (D) α-[2-(2-butoxyethoxy)ethoxy]-4,5-methylenedioxy-2-propyltoluene (piperonyl butoxide).

Of these, the compounds (A), (B) and (C) are more preferable, and the compound (A) is most preferable.

The amount used of the synergist(s) is usually within 1 to 10 times the amount used of the pyrethroid active ingredient (s) by weight.

The snake-controlling agent of the present invention is effective against

*Infraorder scolecophidia* such as Typhlopidae and Leptotyphlopidae, *Infraorder henophidia* such as Boidae, and *Infraorder caenophidia* such as Xenoderminae, Calamarinae, Lycodontinae, Xenodontinae, Colubrinae (e.g. *Elaphe quadrivirgata* and *E. climacophora*), Natricinae (e.g. *Rhabdophis tigrinus*), Viperinae, Crotalinae (e.g. *Agkistrodon blomhoffii, Trimeresurus flavoviridis* and *Crotalus adamanteus*), and Elapidae (e.g. *Naja atra*).

The dosage rate of the pyrethroid compound used as an active ingredient for the snake-controlling agent of the present invention is usually between 0.1 g and 100 g per snake, preferably between 0.5 g and 10 g per snake. When the pyrethroid compound is formulated into an emulsifiable concentrate, the emulsifiable concentrate is used after having been diluted with water so as to have a concentration of the pyrethroid compound within the range of from 0.001 to 10%. When the pyrethroid compound is formulated into an aerosol, a liquefied carbon dioxide gas formulation, a dust, an oil formulation, a fumigant or a smoking formulation, these formulations are applied as they are without dilution.

The above-described dosage rate and concentration vary depending on the application conditions such as the type of the formulation, the time, place and method of the application and the kind of snake. They can be increased or decreased independently of the above-described ranges.

The present invention is illustrated in more detail with reference to the following Examples; however the present invention should not be interpreted as being limited thereto. Parts are by weight.

First, formulation examples will be shown. The active ingredients are indicated by the above compound number and the synergists are indicated by the above compound symbol.

FORMULATION EXAMPLE 1

0.3 Part of each of Compound (2), (4), (9), (15) and (25) is dissolved in 59.7 parts of deodorized kerosene. The resulting mixture is charged in an aerosol container. A valve part is attached to the container. Thereafter, 40.0 parts of liquefied propane gas as a propellant is compressed into the container under pressure through the valve part. Thus, oil aerosols containing 0.3% of each of the active ingredients are obtained.

FORMULATION EXAMPLE 2

0.3 Part of Compound (2) and 0.9 part of Compound (A) are dissolved in 58.8 parts of deodorized kerosene. The resulting mixture is charged in an aerosol container. A valve part is attached to the container. Thereafter, 40.0 parts of liquefied propane gas as a propellant is compressed into the container under pressure through the valve part. Thus, an oil aerosol containing 0.3% of the active ingredient is obtained.

FORMULATION EXAMPLE 3

1.0 Part of Compound (2) and 3.0 part of Compound (A) are dissolved in 56.0 part of deodorized kerosene. The resulting mixture is charged in an aerosol container. A valve part is attached to the container. Thereafter, 40.0 parts of the liquefied propane gas as a propellant is compressed into the container under pressure through the valve part. Thus, an oil aerosol containing 1% of the active ingredient is obtained.

FORMULATION EXAMPLE 4

An oil aerosol containing 1% of the active ingredient is obtained by repeating the same procedure as in Formulation Example 3 except that Compound (2) is replaced by Compound (4).

FORMULATION EXAMPLE 5

1.0 Part of Compound (2), 3.4 parts of deodorized kerosene and 1.0 part of surface active agent (Atmos 300, a registered trade name of Atlas Chemical) were mixed and dissolved. The resulting mixture and 50 parts of pure water are charged in an aerosol container. A valve part is attached to the container. Thereafter, 44.6 parts of liquefied propane gas is compressed into the container under pressure through the valve part. Thus, an aqueous aerosol containing 1% of the active ingredient is obtained.

FORMULATION EXAMPLE 6

35 Grams of Compound (2) is charged in a pressure-resistant container. A valve part is attached to the container. Thereafter, 6965 grams of liquefied carbon dioxide gas as a propellant is compressed into the container through the valve part. Thus, a liquefied carbon dioxide gas formulation containing 0.5% of the active ingredient is obtained.

FORMULATION EXAMPLE 7

10 Parts of Compound (2) is dissolved in a mixture of 35 parts of xylene and 35 parts of dimethylformamide. To the resulting mixture are added 14 parts of polyoxyethylene styryl phenyl ether and 6 parts of calcium dodecylbenzenesulfonate and stirred. Thus, an emulsifiable concentrate containing 10% of the active ingredient is obtained.

FORMULATION EXAMPLE 8

1 Part of Compound (2) is dissolved in an appropriate amount of acetone. To the resulting mixture are added 5 parts of fine powders of synthetic hydrated silicon dioxide, 0.3 part of PAP and 93.7 parts of clay. The resulting mixture is stirred and mixed with a juice mixer. Then, acetone is removed by evaporation to obtain a dust containing 1% of the active ingredient.

FORMULATION EXAMPLE 9

0.1 Part of Compound (4) is dissolved in 5 parts of xylene and 5 parts of trichloroethane. The resulting mixture is added to 89.9 parts of deodorized kerosene. Thus, an oil formulation containing 0.1% of the active ingredient is obtained.

FORMULATION EXAMPLE 10

2.0 Parts of Compound (4) and 6.0 parts of Compound (A) are dissolved in 52.0 parts of deodorized kerosene. The resulting mixture is charged in an aerosol container. A valve part is attached to the container. Thereafter, 40.0 parts of liquefied propane gas is compressed into the container under pressure through the valve part. Thus, an oil aerosol containing 2% of the active ingredient is obtained.

FORMULATION EXAMPLE 11

5 Parts of Compound (3) or (8) and 10 parts of Compound (A) are dissolved in 45 parts of deodorized kerosene. The resulting mixture is charged in an aerosol container. A valve part is attached to the container. Thereafter, 40 parts of liquefied propane gas, a propellant, is compressed into the container under pressure through the valve part. Thus, an oil aerosol containing 5% of the active ingredient is obtained.

FORMULATION EXAMPLE 12

2.0 Parts of Compound (8) and 6.0 parts of Compound (A) are dissolved in 52.0 parts of deodorized kerosene. The resulting mixture is charged in an aerosol container. A valve part is attached to the container. Thereafter, 40.0 parts of liquefied propane gas, a propellant, is compressed into the container under pressure through the valve part. Thus, an oil aerosol containing 5% of the active ingredient.

TEST EXAMPLE 1

A mamushi (*Agkistrodon blomhoffii*) having a total length of about 0.6 m and a habu (*Trimeresurus flavoviridis*) having a total length of about 1.5 m were used for the test. Each of the formulations was directly sprayed onto the snakes from a distance of about 2 m. The time of spraying was 1 second for the mamushi and 5 seconds for the habu. After spraying, the snakes were allowed to rest. After 4, 8 and 24 hours, the snakes were observed to determine whether they had been killed. The same test was repeated five times and the results were averaged. Tables 1 and 2 show the results for mamushi and habu, respectively.

TEST EXAMPLE 2

A *Crotalus adamanteus* having a total length of 1.3 m and a *Naja atra* having a total length of 1 m were used for the test. Each of the formulations was directly sprayed onto the snakes from a distance of about 2 m for 5 seconds. After spraying, the snakes were allowed to rest. After 4, 8 and 24 hours, the snakes were observed to determine whether they had been killed. Table 3 shows the results.

TEST EXAMPLE 3

A habu (*Trimeresurus flavoviridis*) having a total length of about 1.5 m was used for the test. The formulation prepared in Formulation Example 12 was directly sprayed onto the snake from a distance of about 2 m for 5 seconds. After spraying, the snake was allowed to rest. The snake was observed to determine whether it had been killed. The same test was repeated three times and the results were averaged. Table 4 shows the results.

TABLE 1

| | Controlling effect for *Agkistrodon blomhoffii* | | | | | |
|---|---|---|---|---|---|---|
| | | Compound | | Mortality (%) | | |
| Test No. | Test compound | concentration (%) | Production method | After 4 hours | After 8 hours | After 24 hours |
| 1 | (4) | 0.3 | Formulation Example 1 | 100 | 100 | 100 |
| 2 | (9) | 0.3 | Formulation Example 1 | 60 | 80 | 100 |
| 3 | (2) | 0.3 | Formulation Example 1 | 100 | 100 | 100 |
| 4 | (2) + (A) | 0.3 + 0.9 | Formulation Example 2 | 100 | 100 | 100 |
| 5*[1] | (A) | 0.9 | | 0 | 20 | 20 |
| 6*[2] | (2) + (A) | 1.0 + 3.0 | Formulation Example 3 | 100 | 100 | 100 |
| 7 | (4) + (A) | 1.0 + 3.0 | Formulation Example 4 | 100 | 100 | 100 |
| 8*[3] | Control | | | 0 | 0 | 0 |

Notes:
*[1] The formulation used in Test No. 5 was prepared as follows: 0.9 Part of Compound (A) was dissolved in 59.1 parts of deodorized kerosene. The resulting mixture was charged in an aerosol container. Then, a valve part was attached to the container. 40.0 Parts of liquefied propane gas as a propellant was compressed through the valve part under pressure to obtain an oil aerosol containing 0.9% of the synergist.
*[2] In Test No. 6, 2 of 5 snakes subjected to the test were killed within an hour.

TABLE 1-continued

Controlling effect for *Agkistrodon blomhoffii*

| Test No. | Test compound | Compound concentration (%) | Production method | Mortality (%) After 4 hours | After 8 hours | After 24 hours |
| --- | --- | --- | --- | --- | --- | --- |

*[3])The control formulation used in Test No. 8 was prepared as follows: 60 Parts of deodorized kerosene was charged in an aerosol container. Then, a valve part was attached to the container. 40.0 Parts of liquefied propane gas as a propellant was compressed through the valve part under pressure to obtain an oil aerosol containing no active ingredient.

TABLE 2

Controlling effect for *Trimeresurus flavoviridis*

| Test No. | Test compound | Compound concentration (%) | Production method | Mortality (%) After 4 hours | After 8 hours | After 24 hours |
| --- | --- | --- | --- | --- | --- | --- |
| 9 | (4) | 0.3 | Formulation Example 1 | 60 | 100 | 100 |
| 10 | (9) | 0.3 | Formulation Example 1 | 60 | 60 | 100 |
| 11 | (2) | 0.3 | Formulation Example 1 | 80 | 100 | 100 |
| 12 | (25) | 0.3 | Formulation Example 1 | 40 | 40 | 60 |
| 13 | (15) | 0.3 | Formulation Example 1 | 40 | 40 | 60 |
| 14 | (2) + (A) | 0.3 + 0.9 | Formulation Example 2 | 100 | 100 | 100 |
| 15*[1]) | (A) | 0.9 | | 0 | 40 | 40 |
| 16*[2]) | (2) + (A) | 1.0 + 3.0 | Formulation Example 3 | 100 | 100 | 100 |
| 17*[2]) | (4) + (A) | 1.0 + 3.0 | Formulation Example 4 | 100 | 100 | 100 |
| 18*[3]) | Control | | | 0 | 0 | 0 |

Notes:
*[1])The formulation used in Test No. 15 was prepared as follows: 0.9 Part of Compound (A) was dissolved in 59.1 parts of deodorized kerosene. The resulting mixture was charged in an aerosol container. Then, a valve part was attached to the container. 40.0 Parts of liquefied propane gas as a propellant was compressed through the valve part under pressure to obtain an oil aerosol containing 0.9% of the synergist.
*[2])100% mortality within 2 hours was observed in Test No. 16 and 80% mortality within 2 hours was observed in Test No. 17.
*[3])The control formulation used in Test No. 18 was prepared as follows: 60 Parts of deodorized kerosene was charged in an aerosol container. Then, a valve part was attached to the container. 40.0 Parts of liquefied propane gas as a propellant was compressed through the valve part under pressure to obtain an oil aerosol containing no active ingredient.

TABLE 3

| Test No. | Test compound | Compound concentration (%) | Production method | Mortality (%) After 4 hours | After 8 hours | After 24 hours |
| --- | --- | --- | --- | --- | --- | --- |
| | | | *Crotalus adamanteus* | | | |
| 19 | (4) + (A) | 2.0 + 6.0 | Formulation Example 10 | 0 | 100 | 100 |
| | | | *Naja atra* | | | |
| 20 | (4) + (A) | 2.0 + 6.0 | Formulation Example 10 | 0 | 100 | 100 |

TABLE 4

| Test No. | Test compound | Compound concentration (%) | Production method | Mortality (%) After 4 hours | After 8 hours | After 24 hours |
| --- | --- | --- | --- | --- | --- | --- |
| | | | *Trimeresurus flavoviridis* | | | |
| 21 | (8) + (A) | 2.0 + 6.0 | Formulation Example 12 | 100 | 100 | 100 |

*: Of the three snakes subjected to the test, one died in 1.5 hours and another died in 3 hours.

According to the present invention, effective snake-controlling is possible with utilizing the snake-controlling property of pyrethroid compounds.

What is claimed is:

1. A method for controlling snakes selected from the group consisting of *Infraorder Scolecophidia, Infraorder Henophilia* and *Infraorder Caenophidia* which comprises applying to the snakes of this group an amount effective for killing snakes of this group of at least one pyrethroid compound.

2. A method for controlling snakes according to claim 1, wherein the pyrethroid compound has a cyclopentenolone skeleton.

3. A method for controlling snakes according to claim 1, wherein the pyrethroid compound is selected from the group consisting of:

2-methyl-4-oxo-3-(2-propynyl)cyclopent-2-enyl chrysanthemate, 2-methyl-4-oxo-3-(2-propenyl)cyclopent-2-enyl chrysanthemate, 2-methyl-4-oxo-3-(2-propenyl)cyclopent-2-enyl 2,2,3,3-tetramethylcyclopropanecarboxylate, and natural pyrethrins.

4. A method for controlling snakes according to claim 1, wherein the snake-controlling agent further comprises at least one synergist selected from the group consisting of:

bis-(2,3,3,3-tetrachloropropyl)ether,

N-(2-ethylhexyl)bicyclo[2.2.1]hept-5-en-2,3-dicarboxyimide, and isobornyl thiocyanoacetate.

5. A method for controlling snakes according to claim 4, wherein the weight ratio of the active ingredient to the synergist is in the range of from 1:1 to 1:10.

6. A method for controlling snakes according to claim 1, wherein the snake-controlling agent is in the form of an aerosol.

7. A method for controlling snakes according to claim 1, wherein the content of the active ingredient is between 0.01 and 20% by weight when a carrier is present.

* * * * *